US009833462B2

(12) United States Patent
Hong et al.

(10) Patent No.: US 9,833,462 B2
(45) Date of Patent: Dec. 5, 2017

(54) PERSIMMON LEAF-DERIVED POLYSACCHARIDE FRACTION HAVING IMMUNE FUNCTION-ENHANCING ACTIVITY AND METHOD PRODUCING THE SAME

(71) Applicant: KOREA FOOD RESEARCH INSTITUTE, Seongnam-si (KR)

(72) Inventors: Hee-Do Hong, Seongnam-si (KR); Young-Chul Lee, Seongnam-si (KR); Young-Chan Kim, Yongin-si (KR); Kyung-Tack Kim, Seoul (KR); Sang-Yoon Choi, Seoul (KR); Young-Kyung Lee, Seongnam-si (KR); Chang-Won Cho, Seoul (KR); Jeonghae Rho, Seongnam-si (KR); Su-Kyung Sung, Incheon (KR); Kwang-Soon Shin, Seongnam-si (KR); Hye-Ryung Park, Seoul (KR); Sun Young Jo, Suwon-si (KR)

(73) Assignee: KOREA FOOD RESEARCH INSTITUTE, Seongnam-si (KR)

( * ) Notice: Subject to any disclaimer, the term of this patent is extended or adjusted under 35 U.S.C. 154(b) by 577 days.

(21) Appl. No.: 14/307,933

(22) Filed: Jun. 18, 2014

(65) Prior Publication Data
US 2014/0302067 A1 Oct. 9, 2014

Related U.S. Application Data

(63) Continuation of application No. PCT/KR2012/010601, filed on Dec. 7, 2012.

(30) Foreign Application Priority Data

Dec. 19, 2011 (KR) .................. 10-2011-0137700

(51) Int. Cl.
| A61K 36/44 | (2006.01) |
| A61K 31/7004 | (2006.01) |
| A61K 31/7008 | (2006.01) |
| A61K 31/7016 | (2006.01) |
| A61K 31/715 | (2006.01) |

(52) U.S. Cl.
CPC ...... *A61K 31/7004* (2013.01); *A61K 31/7008* (2013.01); *A61K 31/7016* (2013.01); *A61K 31/715* (2013.01); *A61K 36/44* (2013.01)

(58) Field of Classification Search
CPC ..................................................... A61K 36/44
USPC ......................................................... 424/774
See application file for complete search history.

(56) References Cited

U.S. PATENT DOCUMENTS

| 5,240,732 | A  | * | 8/1993  | Ueda     | ........................ | A23L 2/38  |
|           |    |   |         |          |                          | 426/435    |
| 6,863,907 | B2 | * | 3/2005  | Kotani   | ..................... | A61K 8/97  |
|           |    |   |         |          |                          | 424/439    |
| 2002/0009503 | A1 | * | 1/2002 | Kotani | ..................... | A61K 8/97  |
|           |    |   |         |          |                          | 424/725    |
| 2007/0286938 | A1 | * | 12/2007 | Saiki | ........................ | A23F 3/10  |
|           |    |   |         |          |                          | 426/597    |
| 2013/0150464 | A1 | * | 6/2013 | Hishikawa | ........... | A61K 31/352 |
|           |    |   |         |          |                          | 514/784    |

FOREIGN PATENT DOCUMENTS

| KR | 10-1995-0006064 | 6/1995 |
| KR | 10-2003-0024111 | 3/2003 |
| KR | 10-2010-0055952 | 5/2010 |
| KR | 10-2010-0114950 | 10/2010 |

OTHER PUBLICATIONS

Jung et al., "Purified Polysaccharide Activating the Complement System from Leaves of *Diospyos kaki* L.", Korean Journal of Food Science and Technology, 2002, pp. 879-884, vol. 34, No. 5, Korea.
Sa. Y. S. et al., "The Anticoagulant Fraction from the Leaves of *Diospyros kaki* L. has an Antithrombotic Activity", Archives of Pharmacal Research, 2005, pp. 667-674, vol. 28, No. 6, Korea.
Duan J. et al., "Structural features of a pectic arabinogalactan with immunological activity from the leaves of Diospyros kaki", Carbohydrate Research, 2003, pp. 1291-1297, vol. 338, Elsevier, available online at <www.sciencedirect.com>.
Yoo et al., "Antioxidative and Antiallergic Effect of Persimmon Leaf Extracts", Korean Journal of Food Science and Nutrition, 2009, vol. 38, No. 12, pp. 1691-1698, Korea.
International Search Report dated Mar. 28, 2013, in International Patent Application No. PCT/KR2012/010601.
Non-Final Office Action dated Oct. 13, 2017 in U.S. Appl. No. 14/371,220.
Duan et al, International Journal of Biological Macromolecules 46; pp. 465-470. (Year: 2010).

* cited by examiner

*Primary Examiner* — Chris R Tate
(74) *Attorney, Agent, or Firm* — H.C. Park & Associates, PLC

(57) ABSTRACT

A persimmon leaf-derived polysaccharide fraction, a preparation method thereof, and use thereof, the persimmon leaf-derived polysaccharide fraction including, based on the total weight of the polysaccharide fraction, 70-90 wt % of neutral sugar and 10-30 wt % of uronic acid.

7 Claims, 8 Drawing Sheets

[FIG.1]
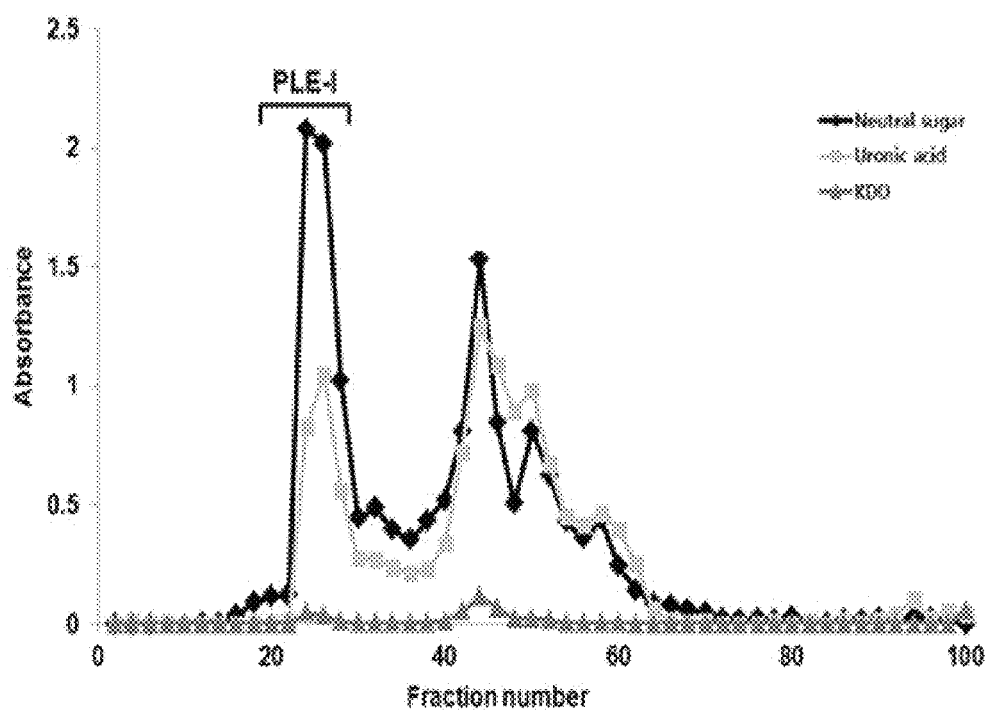

[FIG. 2]
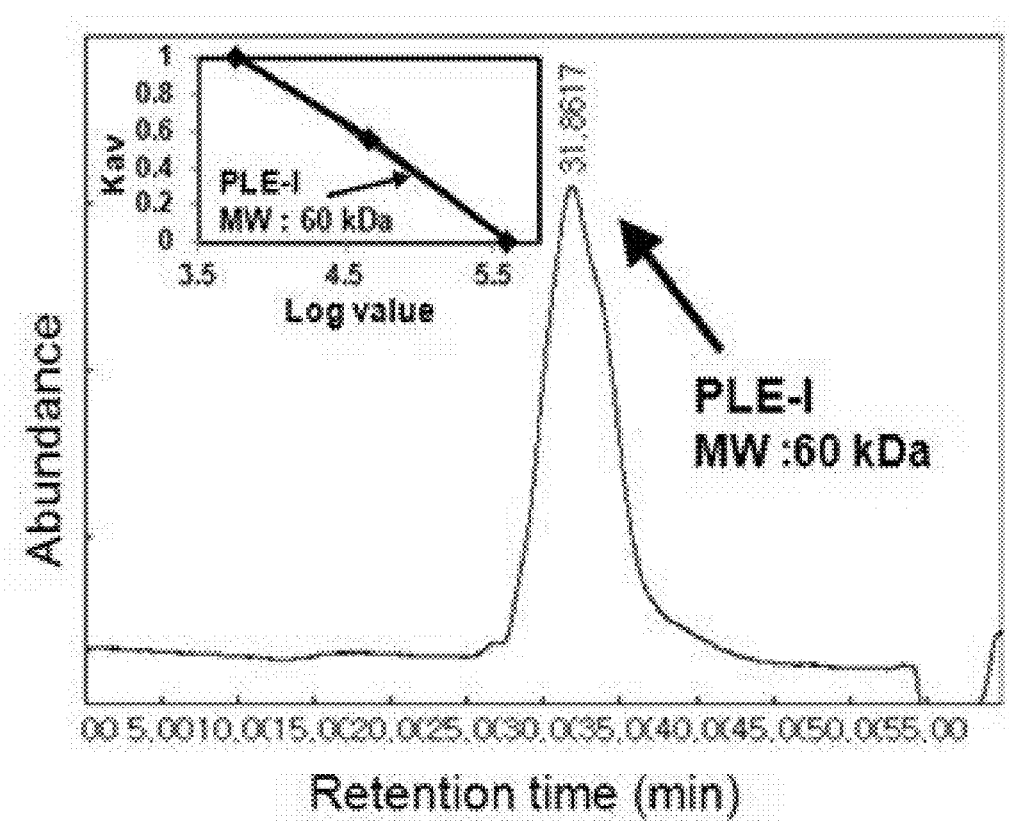

[FIG. 3]
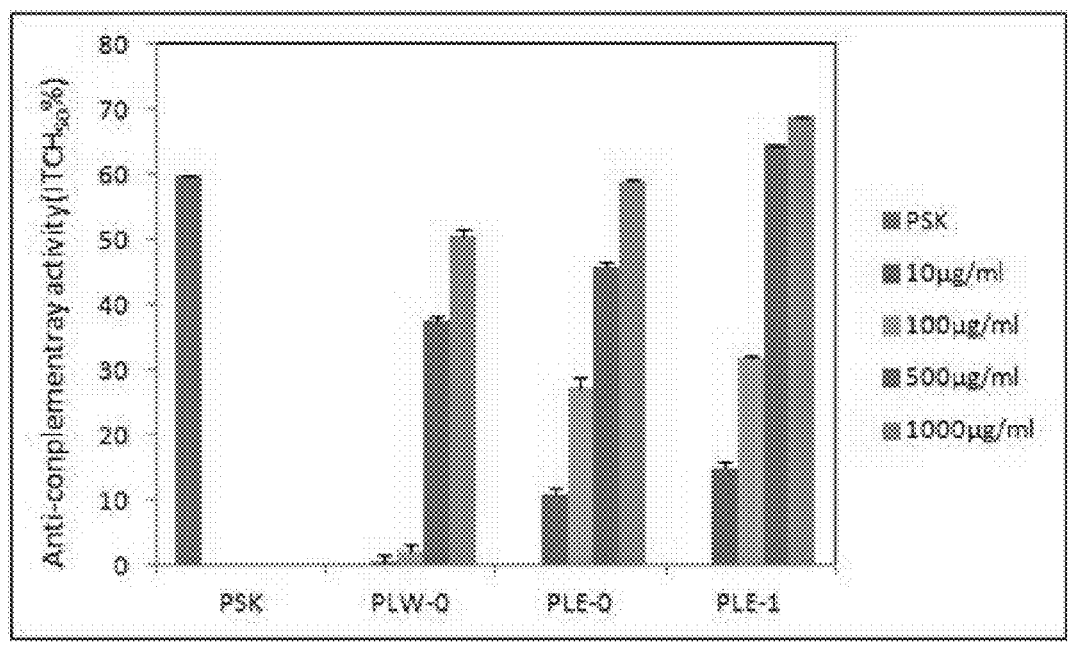

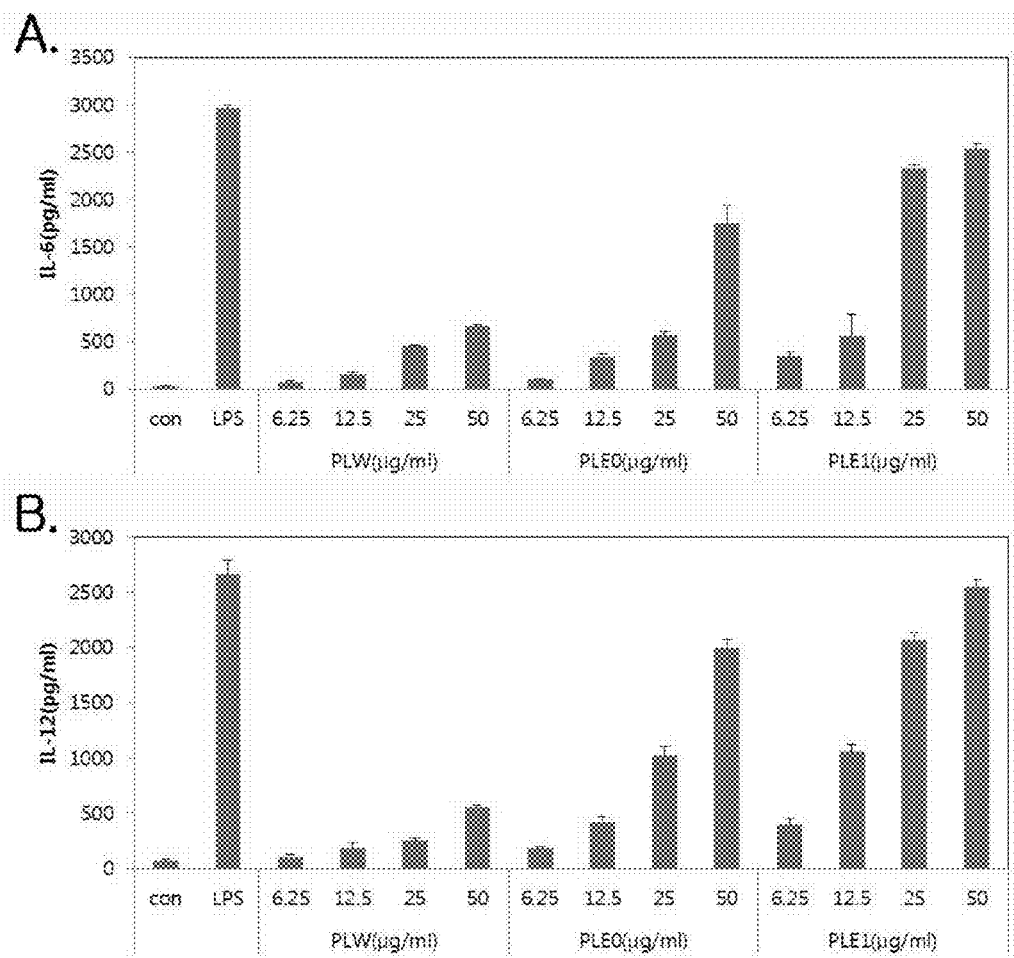
[FIG. 4]

[FIG. 5]
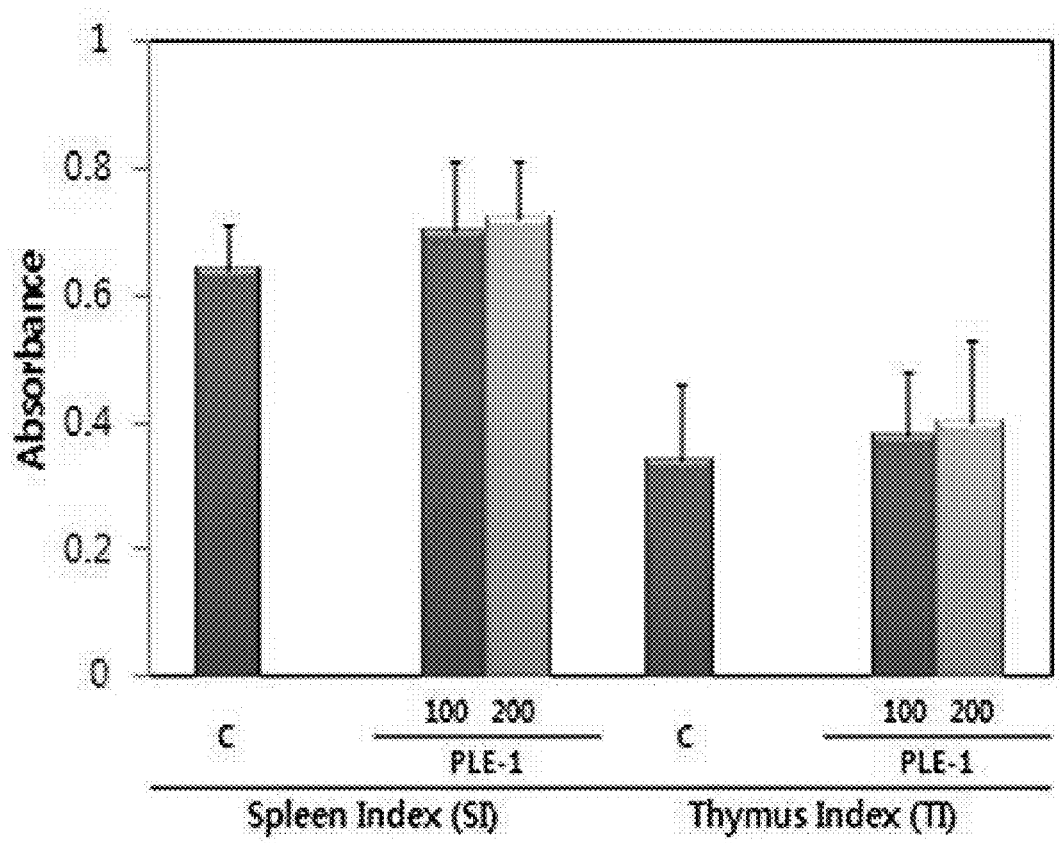

[FIG.6]
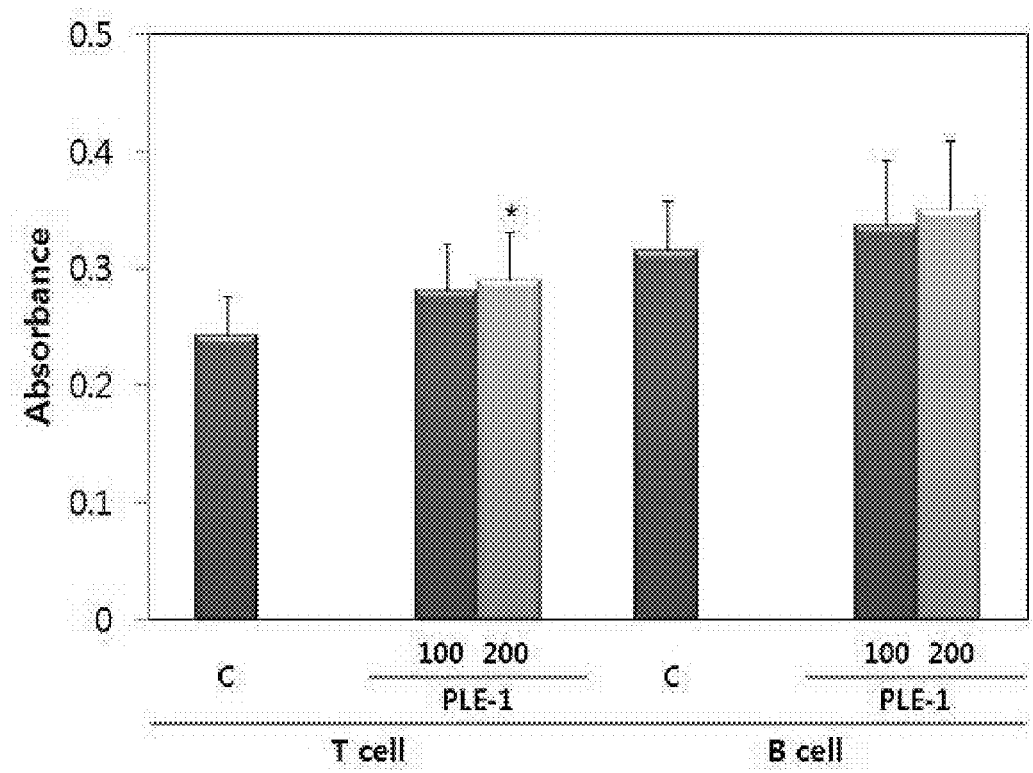

【FIG.7】
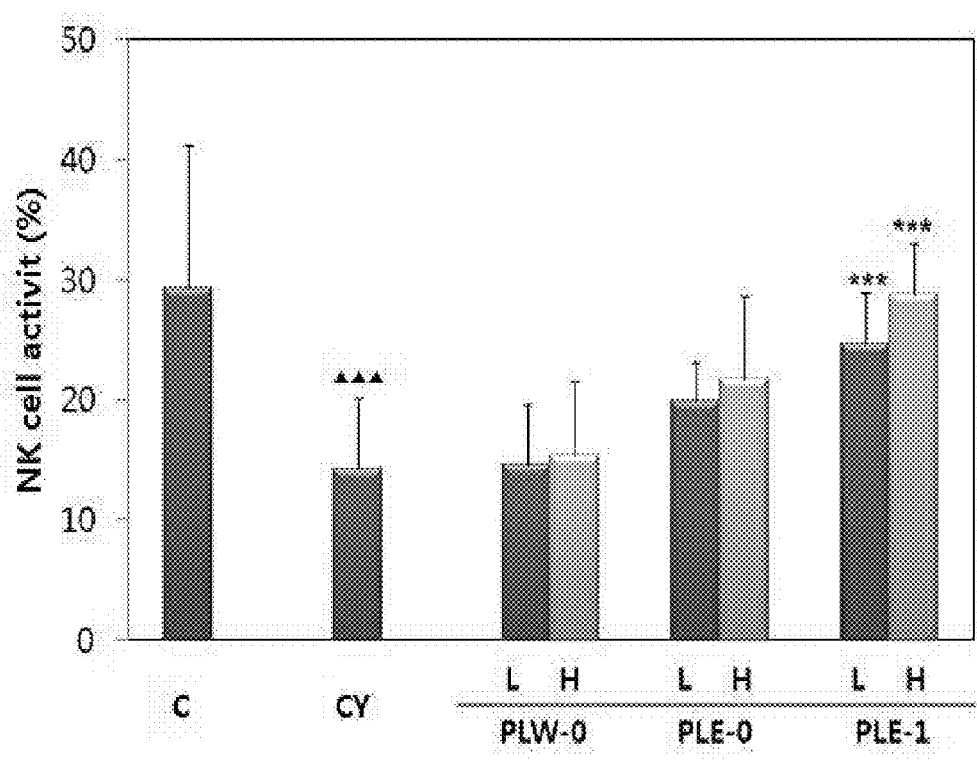

[FIG. 8]
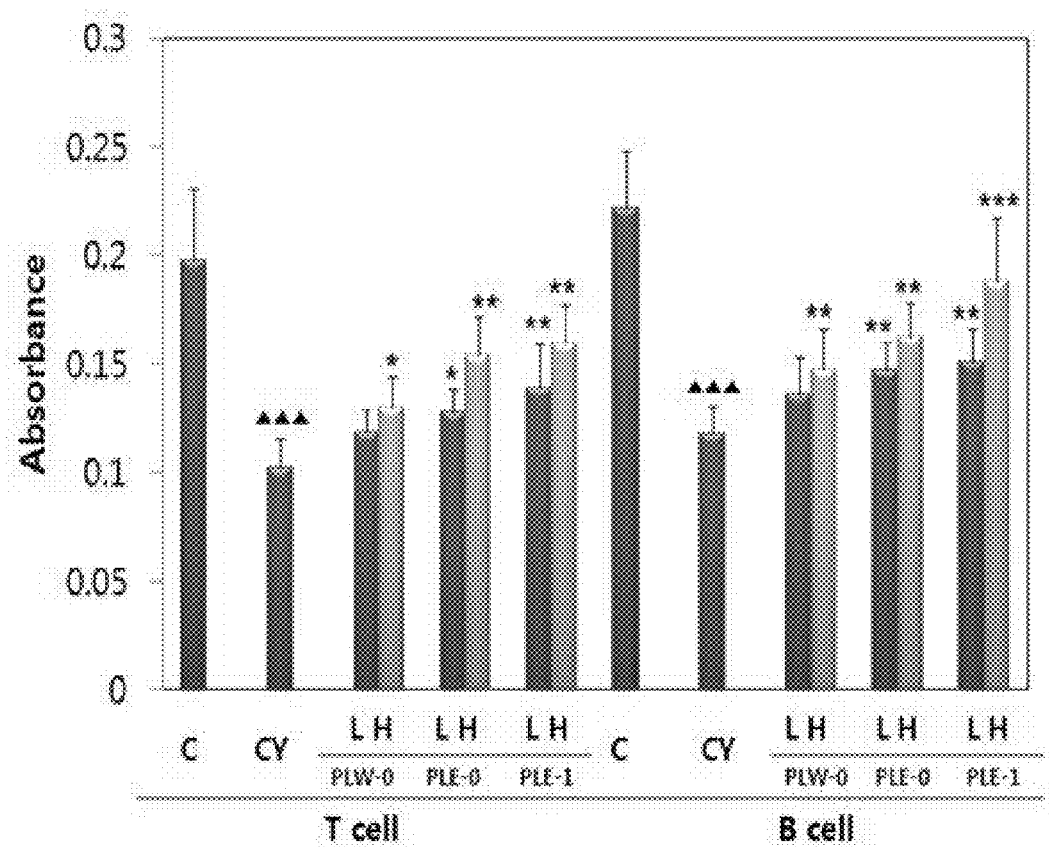

PERSIMMON LEAF-DERIVED POLYSACCHARIDE FRACTION HAVING IMMUNE FUNCTION-ENHANCING ACTIVITY AND METHOD PRODUCING THE SAME

CROSS REFERENCE TO RELATED APPLICATIONS

This application is a continuation of International Application No. PCT/KR2012/010601, filed on Dec. 7, 2012, which claims priority from and the benefit of Korean Patent Application No. 10-2011-0137700, filed on Dec. 19, 2011, all of which are hereby incorporated by reference for all purposes as if fully set forth herein.

BACKGROUND

Field

The present invention relates to a persimmon leaf-derived polysaccharide fraction and a preparation method thereof and more particularly, to a persimmon leaf-derived polysaccharide fraction comprising 70-90 wt % (based on the total weight of the polysaccharide fraction) of neutral sugar and 10-30 wt % (based on the total weight of the polysaccharide fraction) of uronic acid, a preparation method and a use thereof.

Discussion of the Background

Persimmon leaves have a vitamin C content that is 20 times higher than that of a lemon, and thus, are used as health tea. Persimmon leaves have the benefits of facilitating blood circulation, strengthening blood vessels, and being effective against scurvy, anemia, heart diseases, arteriosclerosis and cerebral hemorrhage. However, there have been little or no studies on the effects of persimmon leaves on the immune system.

The complement system is the primary immune system and is known to be activated by the following three pathways: a classical pathway which is activated by the binding of antigen-antibody complexes to C1q; an alternative pathway in which factor B and factor D are involved with C3b existing in blood and which is non-specifically triggered by activators such as lipopolysaccharide and endotoxin; and a lectin pathway which is activated by lectin that binds specifically to mannose in the cell wall.

Natural materials known to be involved in the activation of the complement system include lentinan isolated from *Lentinus edode*, polysaccharide K (PSK) isolated from *Coliolus versicolar*, etc.

Korean Patent Application Laid-Open Publication No. 10-2003-0024111 discloses a composition for lowering blood lipid levels, which comprises a persimmon leaf extract and is used to lower blood lipid levels and protect liver functions. In addition, a paper on the antioxidant and anti-allergic effects of a persimmon leaf extract (Journal of Food Science and Nutrition, 2009, Vol. 38, No. 12, 1691-1698) was published. However, neither the immune-enhancing effect of a persimmon leaf, nor a polysaccharide having a sugar composition disclosed by the present inventors, has been known so far.

SUMMARY

The present inventors have conducted studies on a novel method capable of enhancing immune function, and as a result, have found that a persimmon leaf-derived polysaccharide fraction comprises a polysaccharide having a specific monosaccharide composition and is excellent in enhancing immune function by enhancing the activity of the complement system.

Therefore, it is an object of the present disclosure to provide a persimmon leaf-derived polysaccharide fraction comprising 70-90 wt % (based on the total weight of the polysaccharide fraction) of neutral sugar and 10-30 wt % (based on the total weight of the polysaccharide fraction) of uronic acid.

Another object of the present invention is to provide a food for enhancing immunity, which comprises the polysaccharide fraction as an active ingredient.

Still another object of the present disclosure is to provide a pharmaceutical composition for preventing or treating a disease caused by decreased immunity, which is selected from the group consisting of colds, allergic diseases, and chronic fatigue, the composition comprising the polysaccharide fraction as an active ingredient.

Still another object of the present disclosure is to provide a method for preparing the persimmon leaf-derived polysaccharide fraction, the method comprising treating a persimmon leaf powder with pectinase.

Exemplary embodiments of the present disclosure provide a persimmon leaf-derived polysaccharide fraction comprising 70-90 wt % (based on the total weight of the polysaccharide fraction) of neutral sugar and 10-30 wt % (based on the total weight of the polysaccharide fraction) of uronic acid.

The present disclosure also provides a food composition for enhancing immunity, which comprises the polysaccharide fraction as an active ingredient.

Exemplary embodiments of the present disclosure also provide a pharmaceutical composition for preventing or treating a disease caused by decreased immunity, which is selected from the group consisting of cold, an allergic disease and chronic fatigue, the composition comprising the polysaccharide fraction as an active ingredient.

Exemplary embodiments of the present disclosure also provide a method for preparing the persimmon leaf-derived polysaccharide fraction, the method comprising treating a persimmon leaf powder with pectinase.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the principles of the invention.

FIG. 1 shows the results of gel filtration chromatography for the persimmon leaf-derived crude polysaccharide PLE-0 fraction (Ordinate: Absorbance; Abscissa: Fraction number).

FIG. 2 shows the results of measuring the molecular weight of PLE-I (Ordinate: Abundance; Abscissa: Retention time (min)).

FIG. 3 shows the results of measuring the anti-complementary activity of the persimmon leaf-derived polysaccharide fraction (Ordinate: Anti-complementary activity (ITCH50%); PSK (polysaccharide K): positive control; PLW-O: crude polysaccharide obtained by hot-water extraction; PLE-O: crude polysaccharide treated with Pectinase™; PLE-I: a first fraction obtained by gel filtration chromatography of PLE-O; 10 ug/ml-1000 ug/ml: concentration of each sample in distilled water).

FIG. 4A shows the results of measuring the ability of the persimmon leaf-derived polysaccharide fraction to stimulate the secretion of cytokine IL-6 from macrophages (con: control; LPS: lipopolysaccharide (positive control); PLW-O: crude polysaccharide obtained by hot-water extraction; PLE-O: crude polysaccharide treated with Pectinase™; PLE-I: a first fraction obtained by gel filtration chromatography of PLE-O).

FIG. 4B shows the results of measuring the ability of the persimmon leaf-derived polysaccharide fraction to stimulate the secretion of cytokine IL-12 from macrophages (con: control; LPS: lipopolysaccharide (positive control); PLW-O: crude polysaccharide obtained by hot-water extraction; PLE-O: crude polysaccharide treated with Pectinase™; PLE-I: a first fraction obtained by gel filtration chromatography of PLE-O).

FIG. 5 shows the results of examining whether the persimmon leaf-derived polysaccharide fraction influences the spleen index (SI) and thymus index (TI) in normal mice (c: control; 100 and 200: dose (mg/kg) of PLE-I administered orally to mice).

FIG. 6 shows the results of examining whether the persimmon leaf-derived polysaccharide fraction influences the proliferation of spleen cells, i.e. T cells and B cells in normal mice (c: control; 100 and 200: dose (mg/kg) of PLE-I administered orally to mice).

FIG. 7 shows the results of measuring the effect of the persimmon leaf-derived polysaccharide fraction on the activity of NK cells in immunosuppressed mice (c: normal control group; CY: control group immunosuppressed by cyclophosphamide; L: immunosuppressed mice group administered with 100 mg/kg of PLE-I; H: immunosuppressed mice group administered with 200 mg/kg of PLE-I).

FIG. 8 shows the results of examining whether the persimmon leaf-derived polysaccharide fraction influences the proliferation of T cells and B cells (spleen cells) in immunosuppressed mice (c: normal control group; CY: control group immunosuppressed by cyclophosphamide; L: immunosuppressed mice group administered with 100 mg/kg of PLE-I; H: immunosuppressed mice group administered with 200 mg/kg of PLE-I).

DETAILED DESCRIPTION OF ILLUSTRATED EMBODIMENTS

The present disclosure provides a persimmon leaf-derived polysaccharide fraction comprising 70-90 wt % (based on the total weight of the polysaccharide fraction) of neutral sugar and 10-30 wt % (based on the total weight of the polysaccharide fraction) of uronic acid.

The uronic acid may be one or of galacturonic acid and glucuronic acid.

Moreover, the neutral sugar may comprise one or more of rhamnose, fucose, arabinose, xylose, mannose, galactose and glucose. More specifically, the neutral sugar in the persimmon leaf-derived polysaccharide fraction may comprise, based on the total mole of the neutral sugar in the polysaccharide fraction, 10-18 mole % of rhamnose, 1-5 mole % of fucose, 18-28 mole % of arabinose, 5-15 mole % of xylose, 1-5 mole % of mannose, 30-40 mole % of galactose, and 5-15 mole % of glucose.

The neutral sugar may further comprise 2-methylfucose, 2-methylxylose, apiose and/or aceric acid.

The major components of the polysaccharide fraction were analyzed, and as a result, it was shown that the hydrolysate comprises 71.3-78.6 wt % (based on the total weight of the hydrolysate) of neutral sugar and 16.7-26.2 wt % (based on the total weight of the hydrolysate) of uronic acid. When these values are converted into values for the polysaccharide fraction, the content of neutral sugar in the polysaccharide fraction is 71.8-81.7 wt %, while the content of uronic acid in the polysaccharide fraction is 17.4-26.3 wt % (See Example 4-2 and Table 3).

Also, the polysaccharide fraction may be prepared by a method comprising treating a persimmon leaf powder with pectinase. The preparation method may further comprise collecting a fraction having a molecular weight of 30-100 kDa from the enzymatic hydrolysate of the persimmon leaf powder. The enzymatically treated persimmon leaf powder and the method for preparing the polysaccharide fraction will be described in detail below.

Further, the polysaccharide fraction according to the present invention has an excellent immunity-enhancing effect. This effect of the polysaccharide fraction is described in the following examples of the present disclosure.

In the present disclosure, the anti-complementary activities of a crude polysaccharide extract obtained by hot-water extraction, and enzymatically treated fractions, were measured by the Mayer method. As a result, it was found that the fraction treated with pectinase had the highest activity. The polysaccharide extract treated with pectinase showed an anti-complementary activity, which was 12.5-22% higher than that of a negative control (crude polysaccharide extract) and was higher than that of the positive control PSK (See Example 2). Thus, fractions were prepared using pectinase and subjected to the following experiments.

The anti-complementary activities of the positive control PSK (polysaccharide K; concentration: 1,000 ug/ml), polysaccharide fractions (concentrations; 10, 100, 500 and 1000 ug/ml) obtained by hot-water extraction, polysaccharide fractions (PLE-O; concentrations: 10, 100, 500 and 1000 ug/ml) treated with Pectinase™, polysaccharide extracts (PLE-I; concentrations: 10, 100, 500 and 1000 ug/ml) obtained by extracting PLE-O by gel filtration chromatography, etc., were measured by the Mayer method. As a result, it was found that, at a concentration of 1000 ug/ml that was equal to that of the positive control (PSK), PLE-O, among the polysaccharide fractions showed activity similar to that of the positive control, and PLE-I, showed higher activity than that of the positive control (See Example 5).

In addition, whether the fractions stimulated the secretion of cytokines (IL-6 and IL-12) from macrophages was examined. As a result, it was shown that the PLE-I fraction increased the secretion of cytokines as compared to PLE-0 and PLW, and this increase in the secretion was dependent on the concentration of the polysaccharide fraction (See Example 6 and FIG. 4).

IL-6 and IL-12 are typical cytokines that are induced by macrophages. It is known that these cytokines play a crucial role in inflammatory responses caused by bacterial infection and the levels thereof increase in inflammatory diseases. IL-6 is a cytokine, also called "B-cell stimulating factor 2 (BSF2)" or "interferon β2". IL-6 was found to be a differentiation factor involved in the activation of B lymphocytes (Hirano, T. et al., Nature, 324, 73-76, 1986), and since then, was found to be a multifunctional cytokine that influences the functions of various cells (Akira, S. et at, Adv. in Immunology, 54, 1-78, 1993).

In addition, whether the fraction had the ability to induce the proliferation of immune cells was tested in normal mice. As a result, it was found that the spleen index (SI) and thymus index (TI) of a group treated with the polysaccharide fraction were higher than those of a control group, while the proliferation of T cells and B cells, which constitute spleen cells, in the group treated with the polysaccharide fraction, was higher than that in a negative control group. Particularly, the proliferation of T cells was significantly higher in the test group administered with 200 mg/kg of the polysaccharide fraction than in the control group (See Example 7 and FIGS. 5 & 6).

The spleen is a major immune response region against blood bourn antigens and is a major lymph organ in which the growth of B and T lymphocytes and the differentiation of lymphocytes by the stimulation of antigens occur. The proliferation of lymphocytes in the spleen is very important to the immune system.

The abilities of the polysaccharide fraction to induce the proliferation of spleen cells (T cells and B cells) and enhance the activity of NK cells were measured in mice immunosuppressed by cychlophosphamide. The activity of NK cells was not significantly stimulated by PLW, whereas it was significantly stimulated by PLE-I. Also, it can be seen that PLE-I has an excellent ability to induce the proliferation of spleen cells (T cells and B cells) (See Example 8 and FIGS. 7 & 8).

Cyclophosphamide is known as a typical drug that is used to inhibit rejection responses after malignant tumor treatment or an organ transplant. However, cyclophosphamide has non-selective toxicity, and thus, shows toxicity in not only cancer cells, but also normal cells, causing side effects such as a decrease in leukocytes, a decrease in platelets, and anemia. For this reason, studies have recently been conducted to discover materials capable of minimizing such side effects or immunotoxocity.

Natural killer (NK) cells function to directly attack and kill cancer cells or virus-infected cells through various mechanisms. NK cells make up a small portion (5-10%) of total lymphocytes, but have a potent function of sensing and removing abnormalities such as mutated cells. In addition, NK cells play a very important role in regulating the functions of immune cells, such as stimulating innate and acquired immune cells to perform more potent defensive actions. In normal persons, genetic abnormalities and environmental factors are primarily removed by NK cells.

As described above, it was found that the polysaccharide fraction has an excellent immunity-enhancing activity. Because the persimmon leaf-derived polysaccharide extract has excellent immunity-enhancing activity, the use of the polysaccharide fraction of the present invention can provide a food composition for enhancing immunity and a pharmaceutical composition for preventing or treating diseases caused by decreased immunity.

As used herein, the term"immunity enhancing" means increasing the immune response or activity of the immune system in vivo.

Meanwhile, the food composition according to the present invention includes all types of forms such as a functional food, a nutritional supplement, a health food, and a food additive. The food composition may be prepared into various forms by the methods known in the art.

For example, as a health food, a persimmon leaf-derived polysaccharide fraction according to the present invention may be prepared into a tea or juice, or may be prepared into granules, capsules or powder for intake. Also, a conventional active ingredient which is well known as having an activity in enhancing immunity may be mixed with a persimmon leaf-derived polysaccharide fraction, so as to prepare a composition.

Further, for preparing a functional food, a persimmon leaf-derived polysaccharide fraction may be added to beverages (including alcoholic beverages), fruits, and their processed foods (e.g. canned fruit, bottled fruit, jam, marmalade etc.), fishes, meats, and their processed foods (e.g. ham, sausage, corned beef etc.), breads and noodles (e.g. Japanese noodle, buckwheat noodle, ramen, spaghetti, macaroni etc.), fruit juice, drinks, cookies, toffee, dairy products (e.g. butter, cheese etc.), vegetable oil, margarine, vegetable protein, retort food, frozen food, various seasonings (e.g. soybean paste, soybean sauce, sauce etc.).

The said food composition comprises preferably, but is not limited thereto, 0.01 to 50 weight % (based on the total weight of a food product) of the persimmon leaf-derived polysaccharide fraction of the present invention.

As a food additive, the persimmon leaf-derived polysaccharide fraction of the present invention may be prepared into a form of powder or concentrated liquid.

The present disclosure also provides a pharmaceutical composition for preventing or treating diseases caused by decreased immunity, which may be selected from colds, allergic diseases, and chronic fatigue, the composition comprising the polysaccharide fraction as an active ingredient. The expression "disease caused by decreased immunity" means either a disease that is more easily caused by a decrease in immune function as compared to a normal person, or a disease difficult to treat due to a decrease in immune function. The allergic disease may be selected from atopy, asthma, and allergic rhinitis.

In the pharmaceutical composition, the polysaccharide fraction or its pharmaceutically acceptable salt may be contained alone or in a mixture with one or more pharmaceutically acceptable carrier, excipient, or diluent. The persimmon leaf-derived polysaccharide fraction or a pharmaceutically acceptable salt thereof may be used.

The "pharmaceutically acceptable" means that the components present in the composition are physiologically acceptable and usually do not invoke allergic or similar reactions when administered to humans. Preferably, the salt may be an acid addition salt formed from a pharmaceutically acceptable free acid. The free acid may be an organic or inorganic acid. The organic acid may be one or more of citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid, and aspartic acid. The inorganic acid may be one or more of hydrochloric acid, bromic acid, sulfuric acid, and phosphoric acid.

A pharmaceutically acceptable carrier, for example, carriers for the parenteral or oral preparations may be further included. The carriers for the oral preparations may include lactose, starch, cellulose derivatives, magnesium stearate, and stearic acid. The carriers for the parenteral preparations may include water, a suitable oil, saline, aqueous glucose, and glycol Stabilizers or preservatives may be further included. Examples of suitable stabilizers include sodium hydrogen sulfite, sodium sulfite, and ascorbic acid. Examples of suitable preservatives include benzalkonium chloride, methyl- or prophyl-paraben, and chlorobutanol. A list of pharmaceutically acceptable carriers is disclosed in Remington's Pharmaceutical Sciences, 19th ed., Mack Publishing Company, Easton, Pa., 1995.

The pharmaceutical composition for preventing or treating a disease caused by decreased immunity may be administered to mammalians including human beings by various routes. For example, it may be administered via oral or parenteral routes. A parenteral administration includes intravenous, intramuscular, intra-arterial, intramarrow, subdural, intracardiac, transdermal, subcutaneous, intraperitoneal, intranasal, intra-gastrointestinal tract, topical, sublingual, and rectal administrations. The pharmaceutical composition may be preferably administered transdermally. As used herein, the term "transdermal administration" means that the pharmaceutical composition of the present invention is administered into a cell or the skin, thereby rendering the active ingredient as contained in the composition of the present invention delivered into the skin. For instance, the pharmaceutical composition may be prepared into an injectable formulation, and then administered by lightly pricking the skin with a 30 gauge injection needle, or by a direct application onto the skin.

A pharmaceutical composition of the present disclosure may be formulated in the form of oral preparation or parenteral preparation, according to the above described administration routes.

In case of the formulation for oral administration, the composition may be formulated into powders, granules, tablets, pills, sugar-coated tablets, capsules, liquids, gels, syrups, slurries, and emulsions by the methods well known in the art. For example, preparations for oral administration may be obtained in the form of tablets or sugar-coated tablets by mixing an active ingredient with a solid excipient, grinding, and adding appropriate supplemental agents, then manufacturing a form of granular mixture. Examples of suitable excipients are sugars including lactose, dextrose, sucrose, sorbitol, mannitol, xylitol, erythritol, and maltitol; starches including corn starch, wheat starch, rice starch, and potato starch; celluloses including cellulose, methyl cellulose, sodium carboxymethylcellulose, and hydroxypropylmethylcellulose; and fillers including gelatin and polyvinylpyrrolidone. Further, if desired, cross-linked polyvinylpyrrolidone, agar, alginic acid, or sodium alginate may be added as a solutionizer. Still further, the pharmaceutical composition may additionally comprise anti-coagulating agents, lubricants, wetting agents, flavoring agents, emulsifying agents, and/or antiseptics.

In case of a formulation for parenteral administration, it may be prepared into the form of injectable preparations, creams, lotions, ointments, oils, humectant, gels, aerosol, and nasal inhalants according to the methods well known in the art. The above-mentioned formulations are described in Remington's Pharmaceutical Science, 15th Edition, 1975. Mack Publishing Company, Easton, Pa. 18042, Chapter 87: Blaug, Seymour.

A total effective amount of pharmaceutical composition may be administered to a patient in a single dose, or may be administered in multiple doses by a fractionated treatment protocol. The pharmaceutical composition may contain a variable amount of an active ingredient according to the disease severity. The total dose of the polysaccharide fraction may be about 0.01 μg to 1000 mg/kg body weight/day. According to some embodiments, the total dose may be 0.1 μg to 100 mg/kg body weight/day. However, the dose of the polysaccharide fraction may be suitably determined by considering various factors, such as age, body weight, health condition, sex, disease severity, diet, and excretion times of a patient, as well as administration route and frequency. When those factors are considered, skilled persons in the art may determine appropriate dose of the polysaccharide fraction for a certain use as an immunity-enhancing agent. The inventive pharmaceutical composition is be limited in terms of the types of formulation, administration routes, and administration methods, as long as they exert the effect of the present invention.

The present disclosure provides a use of the persimmon leaf-derived polysaccharide fraction for the preparation of an agent for preventing or treating a disease caused by decreased immunity, which is selected from colds, allergic diseases, and chronic fatigue.

The present disclosure provides a method for preventing or treating a disease caused by decreased immunity, which is selected from colds, allergic diseases, and chronic fatigue, the method comprising administering an effective amount of the persimmon leaf-derived polysaccharide fraction to a subject in need thereof.

The allergic disease may be selected from atopy, asthma, and allergic rhinitis.

The persimmon leaf-derived polysaccharide fraction or pharmaceutically acceptable salt thereof may be administered through various routes including oral, transdermal, subcutaneous, intravenous, and intramuscular administration. As used herein, the "effective amount" refers to the amount showing the effect on preventing and treating a disease caused by decreased immunity, upon being administered to a patient. As used herein, the "subject" refers to animals, preferably mammals, particularly mammals including humans. Cells, tissues or organs of an animal origin are also included. The subject may be a patient in need of treatment.

The persimmon leaf-derived polysaccharide fraction or its pharmaceutically acceptable salt may be administered as it is, or may be prepared into various formulations as described above for administration. Preferably, it may be administered until a desired effect, that is, an effect of preventing or treating a disease caused by decreased immunity is attained. The polysaccharide fraction of the present invention or its pharmaceutically acceptable salt may be administered via various routes according to methods known in the art. In other words, it may be administered orally or parenterally, for example, buccally, intramuscularly, intravenously, intracutaneously, intraarterially, intrasseously, intrathecally, intraperitoneally, intranasally, intravaginally, rectally, sublingually or subcutaneously, or may be administered via a gastrointestinal, transmucosal or respiratory route. For example, the polysaccharide fraction or its pharmaceutically acceptable salt may be directly applied to the skin. Alternatively, the polysaccharide fraction may be prepared into an injectable formulation, and then injected in a predetermined amount into a subcutaneous layer with a 30 gauge thin injection needle, or administered by lightly pricking the skin with the injection needle. According to some embodiments, it may be directly applied to the skin. Also, the polysaccharide fraction or its pharmaceutically acceptable salt may be administered into target cells or tissues (e.g., skin cells or skin tissues) by binding to a molecule causing high affinity-binding or being capsulated within the molecule. The polysaccharide fraction or its pharmaceutically acceptable salt may be bound to a sterol (e.g., cholesterol), a lipid (e.g., cationic lipid, virosome or liposome), or a target cell specific binding agent (e.g., ligand recognized by a target cell specific receptor), through the techniques known in the art. As a suitable coupling agent or a cross-linking agent, for example, protein A, carbodiimide, N-succinimidyl-3-(2-pyridyldithio)propiotate (SPDP), or the like, may be included. These formulations are disclosed in general reference for pharmaceutical chemistry (*Remington's Pharmaceutical Science,* 15th Edition, 1975, Mack Publishing Company, Easton, Pa.).

In addition, the present disclosure provides a method for preparing the persimmon leaf-derived polysaccharide fraction, the method comprising treating a persimmon leaf powder with pectinase. The preparation method may further comprise collecting a fraction having a molecular weight of 30-100 kDa from the enzymatic hydrolysate of the persimmon leaf powder.

In order to prepare the persimmon leaf-derived polysaccharide fraction, a persimmon leaf powder is treated with pectinase. In order to find the most suitable enzyme to prepare an immunoactive material from persimmon leaf powder, crude polysaccharide fractions obtained by hot-water extraction were treated with various enzymes, and the anti-complementary activities of the polysaccharide fractions were measured. As a result, it was found that pectinase is the most suitable enzyme (See Example 2 and Table 1).

Pectinase may be added in amounts of 1-20 wt %, 5-15 wt %, or 10 wt %, based on the weight of the persimmon leaf powder. The persimmon leaf powder that is treated with the enzyme may be suspended in distilled water at a ratio of about 1:5-15 (w/v). Treatment with the hydrolytic enzyme is preferably performed for 1-5 days, and more preferably 2-4 days. Also, the treatment is preferably performed at a pH of 3.5-5.5. The preparation method further comprises, after treatment with the enzyme, a step of heating the remaining pectinase at a temperature of 90-110° C., for 10-60 minutes, to inactivate the enzyme. Due to the heating, soluble polysaccharides can be removed. Due to the heating, the elution of soluble polysaccharide components is increased, and some polymer proteins contained as impurities are modified and precipitated, thereby facilitating the collection of the polysaccharide extract by centrifugation and increasing the purity of the polysaccharide extract.

In addition, the preparation method may comprise, before treatment with the enzyme, decolorizing the persimmon leaf powder. A solvent that is used in the decolorizing step may be any decolorizing solvent that is safe and approved for use in the human body. The decolorizing solvent may be ethanol, potassium sulfite, sodium sulfite, sulfur dioxide, or benzoylperoxide.

The preparation method may additionally comprise a step of collecting a fraction having a molecular weight of 30-100 kDa from the enzymatic hydrolysate of the persimmon leaf powder. The additional step is a step of collecting a fraction having a molecular weight of 30-100 kDa from a polysaccharide extract obtained by separating the residue by a method such as centrifugation or filtration after treatment with the enzyme. The fraction can be collected by any known purification process performed based on a molecular weight. The fraction can be collected by ultrafiltration or gel filtration chromatography. The resulting polysaccharide fraction may be in the form of extract, concentrate, powder, or the like.

It was found that a fraction having a molecular weight of 60 kDa (referred to as PLE-I) after treatment with pectinase also has immunity-enhancing activity. The molecular weight of the collected polysaccharide fraction may be 30-100 kDa, 40-90 kDa, or 50-80 kDa.

The preparation method may further comprise a step of purification by adding a 50-100% alcohol having 1-4 carbon atoms to the resulting polysaccharide fraction, to remove low-molecular-weight materials and impurities.

Accordingly, the present disclosure provides a persimmon leaf-derived polysaccharide fraction comprising, based on the total weight of the polysaccharide fraction, 70-90 wt % of neutral sugar and 10-30 wt % of uronic acid; a preparation method and a use thereof.

The polysaccharide fraction enhances the activity of the complement system and enhances immune function in both normal mice and immunosuppressed mice. Thus, the polysaccharide fraction is effective for the preparation of a competitive food composition and a competitive drug for enhancing immunity.

Hereinafter, the present disclosure will be described in further detail with reference to examples. It is to be understood, however, that these examples are for illustrative purposes only and are not to limit the scope of the present invention.

Example 1: Preparation of Crude Polysaccharide Fraction (PLW-0) from Persimmon Leaves by Hot-Water Extraction and Treatment with Various Enzymes In this example, persimmon leaves in powder form, produced in Yeong-cheon, Gyeongsangbuk-do, Korea and purchased from Baek-Jang-Saeng Co. Ltd. (Korea), were used. The powder was added to 90% ethanol at a ratio of 1:10 (w/v), stirred for 48 hours, filtered, and dried, followed by decolorization.

The decolorized dry powder was suspended in distilled water at a ratio of 1:10 (w/v) and heated at 100° C. for 3 hours. The hot-water extract was centrifuged at 4° C. and 6,500×g, for 15 minutes, and the supernatant was added to a four-fold volume (v/v) of 80% ethanol and allowed to stand for 24 hours to precipitate polysaccharide. The precipitated polysaccharide was subjected to dialysis (molecular weight cut-off: 6,000-8,000) to obtain a hot-water-extracted crude polysaccharide fraction (PLW-0).

The decolorized dry powder was suspended in distilled water (pH 4) at a ratio of 1:10 (w/v), and the suspension was treated with each of commercial enzymes, Econitase™, Rapidase™, Viscozyme™, Celluclast™ 1.5L, Pectinex™, Rohament™ CL, UltrafloL™, Cytolase™ PCL 5 and Pectinase™ (added in an amount of 0.5 wt % based on the weight of the powder), followed by ethanol precipitation and dialysis, thereby obtaining crude polysaccharide fractions (PLE-0-E1 to PLE-0-E9) according to each enzyme.

Example 2: Selection of the Most Suitable Enzyme by Measuring the Activation of Complement System Anti-complementary activity was measured using the Mayer method, by a complement fixation test, based on the hemolysis of red blood cells by a complement remaining after the consumption of the complement by a sample. Specifically, a sample was dissolved in distilled water at various concentrations (10, 100, 500, and 1,000 ug/mL). 50 uL of each of normal human serum (NHS) and GVB++ (gelatin veronal buffered saline, pH 7.4; containing 2% gelatin, 500 uM Ca++, 2 mM Mg++) buffer were mixed with the sample. The mixture was reacted with the sample at 37° C., for 30 minutes, and 350 uL of GVB++ was added thereto, after which the mixture was 10-160-fold serially diluted. To each dilution, 750 uL of GVB+ was added, and then 250 uL of IgM-sensitization sheep erythrocytes (EA cells, 1×10$^8$ cells/mL) were added thereto and allowed to react at 37° C. for 60 minutes. Then, 2.5 mL of PBS was added to stop the reaction. The reaction solution was centrifuged at 2,500 rpm for about 10 minutes, and the absorbance of the supernatant at 412 nm was measured to determine the residual hemolytic activity. NHS was obtained from healthy adults, and as a control, a reaction product between NHS and buffer and distilled water was used. The anti-complementary activity of the polysaccharide was expressed as the inhibition of 50% total complement hemolysis (ITCH$_{50}$, %) relative to the 50% total complement hemolysis (TCH$_{50}$, %) of the control.

The activity of the complement system that plays an important role in an initial immune response was measured at 500 ug/mL for each of the crude polysaccharide fractions, and as a result, it was found that the activities of the fractions with E2, E5, E8 and E9 were relatively high, and the activity of the hot-water-extracted crude polysaccharide fraction was relatively low (see Table 1).

TABLE 1

Results of measurement of anti-complementary activities of polysaccharide fractions treated with enzymes

| | Enzymes | | Persimmon leaves | |
|---|---|---|---|---|
| Type | Product name | Main activity | Sample name | Anti-complementary Activity (ITCH$_{50}$, %, at 500 ug/mL) |
| — | — | — | PSK (Positive control) | 40.1 ± 1.8 |
| 0 | Non-enzymatic treatment | — | PLW-0 | 37.6 ± 1.3 |
| E1 | Econase CE | cellulase | PLE-0-E1 | 30.2 ± 2.8 |
| E2 | Rapidase | pectinase, hemicellulase, cellulase | PLE-0-E2 | 35.4 ± 3.1 |
| E3 | Viscozyme | arabinase, cellulase, -glucanase, hemicellulase, xylanase | PLE-0-E3 | 25.4 ± 1.9 |
| E4 | Celluclast 1.5 L | cellulase | PLE-0-E4 | 31.3 ± 1.7 |
| E5 | Pectinex | pectinase | PLE-0-E5 | 42.3 ± 0.9 |
| E6 | Rohament CL | cellulase | PLE-0-E6 | 29.6 ± 3.1 |
| E7 | Ultraflo L | -glucanase | PLE-0-E7 | 27.4 ± 1.4 |
| E8 | Cytolase PCL 5 | pectinase | PLE-0-E8 | 43.7 ± 1.2 |
| E9 | Pectinase | pectinase | PLE-0-E9 | 45.9 ± 0.6 |

As can be seen from the above results, it is suggested that, when the persimmon leaves were treated with commercial enzymes having pectinase activity, homogalacturonan regions of pectin in the persimmon leaves was degraded by pectinase, rendering immunoactive components easily separated.

Example 3: Preparation of Persimmon Leaf-Derived Polysaccharide Fraction by Enzymatic Treatment The decolorized persimmon leaf powder obtained in the same manner as described in Example 1 was used. The decolorized persimmon leaf powder was suspended in a 10-fold volume (w/v) of distilled water (pH 4), and pectinase (Rapidase C80MAX, Bision Corp.) was added thereto in an amount of 10 wt %, based on the weight of the powder. Then, the solution was enzymatically treated in an incubator at 50° C. for 3 days. Next, the enzymatically treated reaction solution was heated at 101° C. for 30 minutes, to extract soluble polysaccharide and inactivate the remaining pectinase.

After enzymatic treatment, the sample was centrifuged at 4° C. and 6,500 rpm for 15 minutes to remove residue, and was filtered by ultrafiltration to remove fine materials having a molecular weight of 3 kDa or less, thereby obtaining an enzymatically treated crude polysaccharide fraction (PLE-0).

The persimmon leaf-derived crude polysaccharide fraction PLE-0 was loaded onto a Sephadex G-75 column (2.5×90 cm) equilibrated with 50 mM ammonium formate buffer (pH 5.5) and was eluted using the same buffer. As a result, it was found that the persimmon leaf-derived fraction PLE-0 is composed of three fractions having different molecular weights, and the first fraction of the three fractions was named PLE-I (see FIG. 1). The same experiment was repeated 6-7 times to verify the experimental results.

Example 4: Characterization of Persimmon Leaf-Derived Polysaccharide Fraction (PLE-I)

4-1: Measurement of Purity and Molecular Weight

The purity and molecular weight of PLE-I purified from persimmon leaves were analyzed by HPLC.

The analysis was performed using Shimadzu LC 6A equipped with Asahipak GS-320+GS220 (each 0.76×50 cm, Asahi Chemical Industry Co., Japan). 0.2M NaCl was used as an elution solvent, and the molecular weight of the purified polysaccharide was measured by comparison with a standard curve obtained using standard pullulans (P-400, 200, 100, 50, 20 and 5; Showa Denko Co., Japan).

As a result, PLE-I showed a symmetric single peak, suggesting that it has relatively high purity. In addition, the measurement results of the molecular weight using standards (pullulan series) indicated that the molecular weight of PLE-I purified from persimmon leaves was 60 kDa (See FIG. 2).

4-2: Measurement of Sugar Composition of PLE-I

To analyze the sugar composition of PLE-I, hydrolysis was performed according to a slight modification of the method of Albersheim et at, and then each sugar component was derivatized into alditol acetate and analyzed by GC. The polysaccharide sample was hydrolyzed in 2M TFA (trifluoroacetic acid) at 121° C. for 1.5 hours, and the hydrolysate was separated into neutral sugar and acidic sugar by Dowex-1 (acetate form) resin. It was dissolved in 1 mL of 1M NH$_4$OH (ammonia solution) and reduced with 10 mg of NaBH$_4$ for 4 hours. A suitable amount of acetic acid was added thereto to remove the remaining NaBH$_4$. Then, methanol was added thereto, and the solution was repeatedly dried to remove an excess of acetic acid, whereby each sugar component was converted into its corresponding alditol. Then, each alditol was converted into alditol acetate by reacting it with 1 mL of acetic anhydride at 121° C. for 30 minutes. The alditol acetate was separated with a chloroform/H$_2$O$_2$ phase solvent system and extracted, and the extract was dried, and then dissolved in a small amount of acetone and used as a sample for GC analysis. GC analysis of the alditol acetate derivatives was performed under the conditions described in Table 2 below, and the mole % of each sugar component was determined based on the peak area, molecular weight and molecular response factor for FID of each derivative.

TABLE 2

| GC analysis conditions | |
|---|---|
| Apparatus | GC ACME-6100 (YoungCo. Ltd., Anyang, Korea) |
| Detector | Flame ionization detector(FID) (Young-Lin Co. Ltd., Anyang, Korea) |
| Column | SP-2380 capillary column (Supelco, Bellefonte, USA) |
| Column size | 0.25 mm × 30 m, 0.2 m film thickness |
| Oven temp. | 60° C.(1 min) → 220° C.(12 min) → 250° C.(15 min) 30° C./min  8° C./min |

TABLE 2-continued

GC analysis conditions

| | |
|---|---|
| Injector temp. | 250° C. |
| Detector temp. | 270° C. |
| Carrier gas | N2(1.5 mL/min) |

The results of measuring the sugar components of the persimmon leaf-derived crude polysaccharide indicated that the persimmon leaf-derived crude polysaccharide was mainly composed of rhamnose (Rha), arabinose (Ara), galactose (Gal) and galacturonic acid (GalA) (See Table 3).

TABLE 3

Sugar composition of the polysaccharide fraction

| Chemical composition (weight %) | PLW-0 | PLE-0 | PLE-1 |
|---|---|---|---|
| Neutral sugar | 60.4 | 71.3 | 78.6 |
| Uronic acid | 38.3 | 26.2 | 16.7 |
| Protein | 0.0 | 0.7 | 3.8 |
| KDO-like material | 1.3 | 1.8 | 0.9 |
| Components of neutral sugar (mole %) | | | |
| 2-Mefuc | 0.3 | 1.6 | 0.0 |
| Rha | 7.1 | 15.6 | 13.2 |
| Fuc | 1.2 | 2.4 | 2.2 |
| 2-Mexyl | 0.5 | 2.0 | 0.0 |
| Ara | 33.6 | 26.3 | 22.6 |
| Xyl | 5.7 | 6.7 | 10.4 |
| Api | 3.9 | 4.5 | 0.0 |
| Aceric acid | 2.5 | 1.4 | 0.0 |
| Man | 1.2 | 2.1 | 3.0 |
| Gal | 28.6 | 32.3 | 38.0 |
| Glc | 15.5 | 5.1 | 10.5 |

The KDO-liked material indicates 3-deoxy-D-manno-2-octulosonic acid (KDO) and 3-deoxy-D-lyxo-2-heptulosaric acid (DHA), and the uronic acid indicates galacturonic acid and glucuronic acid. The contents of the components of neutral sugar were expressed based on the total weight of neutral sugar.

Example 5: Measurement of Anti-Complementary Activity of Persimmon Leaf-Derived Polysaccharide Fraction In order to examine whether the persimmon leaf-derived polysaccharide fraction activates the complement system that plays an important role in initial defense against infection of the human body, the anti-complementary activity was measured in the manner as described in Example 2.

1,000 ug/ml of PSK (polysaccharide K), which is an immunoactive polysaccharide from *Coriolus versicolor*, was used as a positive control, whereas distilled water containing no sample was used as a negative control. The ability of each sample to activate the complement system was determined based on that of the negative control taken as 0% $ITCH_{50}$.

As a result, it was found that the crude polysaccharide fraction PLE-0 obtained by treatment with pectinase showed greater anti-complementary activity even at low concentration compared to the crude polysaccharide PLW-0 obtained by simple hot-water extraction, while showing the activity similar to that of the positive control (commercial immunoactive polysaccharide PSK) in a concentration-dependent manner. In addition, it was shown that PLE-I obtained by further purifying PLE-0 showed higher activity than PLE-0 (See FIG. 3).

Example 6: Ability of PLE-I to Stimulate Production of Cytokines in Macrophages 2 mL of 5% thioglycollate medium was injected intraperitoneally to a C57BL/6 (female, 6 weeks) mouse, and after 72 hours, macrophages were collected from the mouse. 100 uL of the macrophages were added to each well of a 96-well well culture plate at a concentration of $2.25 \times 10^5$ cells/mL, and then 100 ul of each sample was added thereto at various concentrations, and the cells were cultured in 5% $CO_2$ incubator at 37° C. for 24 hours. After completion of the culture, the cell culture was centrifuged at 1,500 rpm and 4° C. for 5 minutes, and 150 uL of the supernatant was collected and the content of cytokines in the supernatant was measured. The positive control LPS was used at a concentration of 2 ug/mL.

The content of cytokines produced in macrophages was analyzed by sandwich ELISA (enzyme-immunosorbent assay). An antibody for each cytokine was diluted in coating buffer and coated on a flat 96-well microplate, after which it was allowed to stand at 4° C. for 12 hours. The coated microplate was washed three times with washing buffer (PBS with 0.05% tween 20, PBST), and 200 mL of assay diluent (PBS with 10% FBS or 2% skim milk) was added to the plate and allowed to stand for 1 hour to block the surface of wells to which the antibody was not attached. After completion of blocking, each well was washed three times with washing buffer, and 50 mL of each of serially diluted recombinant mouse cytokine and the immune cell culture were added to each well, respectively. The plate was allowed to stand at room temperature for 2 hours, and then washed with washing buffer and treated with 100 mL of detection antibody (in assay diluent). Next, the plate was allowed to stand at room temperature for 1 hour, and then washed again. The plate was treated and reacted with 100 mL of enzyme reagent (avidin peroxidase conjugate) at room temperature for 30 minutes, and then 100 mL of a substrate solution [tetramethylbenzidine (TMB) and hydrogen peroxide] was added thereto and allowed to react in a dark place for 30 minutes. Next, the plate was treated with 50 mL of stop solution [(1 M $H_3PO_4$ or 2N $H_2SO_4$)], and the absorbance at 450 nm was measured (See Saike I et at, Vaccine 6:238-244, 1988).

FIG. 4 shows the results of measuring the production of cytokines in macrophages caused by the direct stimulation of the persimmon leaf-derived polysaccharide sample. As can be seen in FIG. 4, PLE-I stimulated the secretion of IL-6 and IL-12 in a concentration-dependent manner. PLE-I has an excellent ability to stimulate the secretion of cytokines, compared to PLW and PLE-0.

Example 7: Effect on Proliferation of Spleen Immune Cells in Normal Mice 7-1: Preparation of Experimental Animals Experimental animals used in this study were 7-8-week-old male SPF KM mice obtained from the Laboratory Animal Center of Yanbian University. The animals were acclimated in the IVC system of the laboratory for about 5 days with free access to solid feed and water, and then were randomly divided into various test groups, each consisting of 10 animals. The mice were housed at a temperature of 22±2° C. and a humidity of 40-60%, with 12-hr light/12-hr dark cycles. All the polysaccharide samples were administered orally at two doses of 100 mg/kg and 200 mg/kg. A control group was administered orally with distilled water, instead of an aqueous solution of the polysaccharide sample. The polysaccharide sample was administered directly into the stomach for 15 days.

7-2: Measurement of Spleen Index (SI) and Thymus Index (TI)

The spleen was extracted aseptically from the mice scarified by cervical dislocation, and the weights of the spleen and the thymus were measured. Based on the measured values, spleen index (SI) and thymus index (TI) were calculated according to the following equation:

$$\sqrt{\frac{\text{weight of spleen (thymus)} \times 100}{\text{weight of mouse}}}$$

The SI and TI indices are shown in FIG. 5. As can be seen therein, the two indices were higher in the test group administered with PLE-I than in the control group.

7-3: Measurement of the Ability to Induce Proliferation of Immune Cells

The polysaccharide samples administered to the mice for 15 days, and then spleen cells were isolated from the mice by the Mishell method. The spleen was extracted aseptically from the mice scarified by cervical dislocation. The extracted spleen was washed with RPMI 1640 medium and then lightly crushed with a sterile glass rod to isolate cells. A suspension of the isolated cells was passed through a 200 mesh stainless steel sieve, washed twice with the medium, and then centrifuged at 1,000 rpm for 5 minutes. The resulting solids were suspended in distilled water with Tris-buffered ammonium chloride ($NH_4Cl$, pH7.2) for 5 minutes to remove erythrocytes. The erythrocyte-free spleen cells were dispersed in RPMI medium 1640, stained with trypan blue solution, and then counted using a hemocytometer. The cells were dispersed at a concentration of $3.0 \times 10^6$ cells/mL, and then 90 uL of the cells were added to each well of a 96-well plate and used for the measurement of cell proliferation.

ConA and LPS were added to the cells to final concentrations of 5 ug/mL (ConA) and 10 ug/mL (LPS), and after 72 hours, the proliferation of the spleen cells was evaluated by comparison with the absorbance of the control group to which 10% FBS-RPMI 1640 was added.

The results are shown in FIG. 6. As can be seen therein, the proliferation of T cells and B cells was higher in the group administered with PLE-I than in the negative control group. Particularly, the proliferation of T cells was significantly greater in the test group administered with 200 mg/kg of PLE-I than in the control group (ONE WAY-ANOVA, $p<0.10$).

Example 8: Evaluation of Immunity-Enhancing Activity in Immunosuppressed Animal Models 8-1: Preparation of Experimental Animals Experimental animals, administration methods of polysaccharide samples, and doses were the same as described in the method for evaluating the immune function of normal mice as descried above. A control group was administered orally with distilled water once a day, and an immunosuppressed model group was injected intraperitoneally with 100 mg/kg of cyclophosphamide (Cy) once a day for 3 days to suppress the immunity, and then administered orally with distilled water for 14 days. Other test groups were injected intraperitoneally with 100 mg/kg of cyclophosphamide (Cy) once a day for 3 days, and then administered orally with polysaccharide samples in two amounts of 100 mg/kg and 200 mg/kg once a day for 14 days.

24 hours after final administration, the body weight of the mice was measured, and blood was collected from the mice, after which the mice were sacrificed and the spleen and the thymus were extracted therefrom and weighed. Next, the proliferation of spleen cells (T cells and B cells) and the activity of NK cells were measured. The results of the experiment were expressed as mean±SD for each group using SPSS 17.0, and the statistical significance between the groups was analyzed by ONE WAY-ANOVA.

8-2: Measurement of Activity of NK Cells

The activity of NK cells was measured by a modified lactate dehydrogenase (LDH) release assay that measures LDH released from YAC-1 cells (NK-sensitive cell line; cancer cells) disrupted by the attack of NK cells (see Konjevi G. et al, J Immunol Methods; 200(1-2): 199-201, 1997).

YAC-1 cells were added to each well of a 96-hole well U-bottom culture plate (Corning Glass Works, Corning, USA) at a concentration of $1 \times 10^{4/100}$ ul and cultured with the isolated spleen cells, in which the number of the spleen cells was adjusted such that the effector-to-target cell ratio was 50:1. Then, the plate was incubated in a 5% $CO_2$ incubator at a humidity of 90% and a temperature of 37° C. for 4 hours. Next, the cells were centrifuged, and 100 uL of the LDH-released supernatant was collected and transferred to flat-bottom microplates (Nunc, RosRilde, Denmark). An LDH release assay was performed using ELISA (microtiter plate reader, Roche, Mannheim, Germany). Specifically, 100 uL of reagent (LDH substrate mixture) was added to each well and allowed to react at room temperature (15-25° C.) for 30 minutes under a light-shielded condition. Next, 50 ul of stop solution (1N HCl) was added to stop the reaction, and the absorbance at 492 nm was measured. Only medium was added to a well used for the measurement of spontaneous LDH, while, to a maximum LDH well used to examine the maximum value of LDH released from the YAC-1 cells, triton X-100 solution was added to induce the total lysis of the cells. The percentage (%) of cytotoxicity is LDH released from each culture and was calculated using the following equation:

$$NK \text{ cell activity } (\%) = \frac{OD_{experimental} - OD_{spontaneous}}{OD_{maximum} - OD_{spontaneous}} \times 100$$

The results of the measurement are shown in FIG. 7. When the group administered with PLE-I was compared with the immunosuppressed animal group, it was found that the NK cell activity of the group administered with PLE-I was restored to a level similar to that of the normal control group ($p<0.01$).

8-3: Measurement of the Ability to Induce Proliferation of T Cells and B Cells

The proliferation of spleen cells was measured using the same method as described above with respect to the normal mouse models (See Example 7-3).

The results of the measurement are shown in FIG. 8. As can be seen therein, when the group administered with PLE-I was compared with the immunosuppressed animal group administered with cychlophosphamide, PLE-I showed an excellent ability to induce the proliferation of T cells and B cells.

What is claimed is:

1. A persimmon leaf-derived polysaccharide fraction comprising 70-90 wt % of a neutral sugar and 10-30 wt % of a uronic acid, based on the total weight of the polysaccharide fraction,
   wherein the persimmon leaf-derived polysaccharide fraction is prepared by treating a persimmon leaf powder with pectinase,
   wherein the persimmon leaf-derived polysaccharide fraction has a molecular weight of 30-100 kDA after treatment of a pectinase-enzymatic hydrolysate of the persimmon leaf powder,
   wherein the uronic acid comprises at least one selected from the group consisting of galacturonic acid and glucuronic acid, and
   wherein the neutral sugar comprises, based on the total mole of the neutral sugar in the polysaccharide fraction, the following:
   10-18 mole % of rhamnose;
   1-5 mole % of fucose;
   18-28 mole % of arabinose;
   5-15 mole % of xylose;
   1-5 mole % of mannose;
   30-40 mole % of galactose; and
   5-15 mole % of glucose.

2. The persimmon leaf-derived polysaccharide fraction of claim 1, wherein the neutral sugar further comprises 2-methylfucose, 2-methylxylose, apiose, or aceric acid.

3. The persimmon leaf-derived polysaccharide fraction of claim 1, wherein the persimmon leaf-derived polysaccharide fraction enhances an immune response.

4. A composition for enhancing immunity comprising the persimmon leaf-derived polysaccharide fraction of claim 1 as an active ingredient.

5. A method of preparing the persimmon leaf-derived polysaccharide fraction of claim 1 comprising:
   treating persimmon leaf powder with pectinase under suitable conditions to form a hydrolysate; and
   collecting a fraction of the treated leaf powder having a molecular weight of 30-100 kDa from the hydrolysate.

6. A method for treating at least one decreased immunity-caused disease selected from the group consisting of colds, allergic diseases, and chronic fatigue, the method comprising administering an effective amount of the persimmon leaf-derived polysaccharide fraction of claim 1 to a subject in need thereof.

7. The method of claim 6, wherein the allergic diseases are selected from the group consisting of atopy, asthma, and allergic rhinitis.

* * * * *